(12) United States Patent
Waksmundzki et al.

(10) Patent No.: US 7,883,498 B2
(45) Date of Patent: Feb. 8, 2011

(54) ABSORBENT ARTICLE HAVING RE-FASTENABLE CLOSURES

(75) Inventors: Andrew Waksmundzki, Jackson, NJ (US); Carol Erdman, West Chester, PA (US); Frank S. Glaug, Chester Springs, PA (US)

(73) Assignee: First Quality Retail Services, LLC, Great Neck, NY (US)

( * ) Notice: Subject to any disclaimer, the term of this patent is extended or adjusted under 35 U.S.C. 154(b) by 555 days.

(21) Appl. No.: 11/663,896

(22) PCT Filed: Sep. 28, 2005

(86) PCT No.: PCT/US2005/034458

§ 371 (c)(1),
(2), (4) Date: Dec. 12, 2007

(87) PCT Pub. No.: WO2006/039242

PCT Pub. Date: Apr. 13, 2006

(65) Prior Publication Data

US 2008/0132863 A1    Jun. 5, 2008

(51) Int. Cl.
*A61F 13/15* (2006.01)
*B32B 5/00* (2006.01)
(52) U.S. Cl. ............... 604/385.24; 604/385.26; 604/285.27; 604/385.29; 604/387; 604/389; 604/391; 156/177; 156/178; 156/179
(58) Field of Classification Search ............ 604/385.24, 604/385.26, 285.27, 385.29, 387, 389, 391
See application file for complete search history.

(56) References Cited

U.S. PATENT DOCUMENTS

| | | | |
|---|---|---|---|
| 4,381,781 A | | 5/1983 | Sciaraffa et al. |
| 4,894,060 A | * | 1/1990 | Nestegard ............ 604/391 |
| 5,085,655 A | | 2/1992 | Mann et al. |
| 5,300,057 A | | 4/1994 | Miller et al. |
| 5,312,387 A | | 5/1994 | Rossini et al. |
| 5,389,438 A | | 2/1995 | Miller et al. |
| 5,899,896 A | | 5/1999 | Surprise et al. |
| 6,174,303 B1 | | 1/2001 | Surprise et al. |
| 6,454,752 B1 | | 9/2002 | Huang et al. |
| 6,575,949 B1 | * | 6/2003 | Waksmundzki et al. 604/385.11 |
| 6,645,190 B1 | | 11/2003 | Olson |

FOREIGN PATENT DOCUMENTS

| | | |
|---|---|---|
| DE | 198 54 123 | 5/2000 |
| EP | 1 226 802 | 7/2002 |
| EP | 1 350 495 | 10/2003 |
| WO | WO 02/43638 | 6/2002 |
| WO | WO 2005/044560 | 5/2005 |

OTHER PUBLICATIONS

International Search Report and Written Opinion for PCT/US2005/034458 dated Apr. 21, 2006.

* cited by examiner

*Primary Examiner*—Jacqueline F. Stephens
(74) *Attorney, Agent, or Firm*—Amster, Rothstein & Ebenstein LLP

(57) ABSTRACT

Absorbent articles suitable for use as diapers or other hygiene products are provided. The absorbent articles have one or more closure system features including dual elasticity, rear closure, and the use of co-adhesives for the fasteners. Products according to the invention may provide any of several benefits, including a high level of comfort in use, resistance to tampering by the wearer, and relatively quiet attachment and detachment of the closures.

9 Claims, 5 Drawing Sheets of the wearer.

ABSORBENT ARTICLE HAVING RE-FASTENABLE CLOSURES

FIELD OF THE INVENTION

This invention relates to absorbent articles. More particularly, it relates to absorbent articles with closure means providing high performance in terms of at least one of fit, comfort, and resistance to tampering by the wearer.

BACKGROUND OF THE INVENTION

Absorbent articles such as disposable diapers, training pants, adult incontinence garments, and the like are known, their major function being to absorb and contain body exudates. Such articles are thus intended to prevent the soiling, wetting, or other contamination of clothing or other articles, such as bedding, that come in contact with the wearer. In the case of disposable diapers, they typically all have a similar basic structure that includes a liquid permeable topsheet, a liquid impermeable backsheet, an absorbent core positioned between the topsheet and the backsheet, and a means for fastening the diaper about the wearer's waist.

The means for fastening has typically included tabs mounted on the rear section of the absorbent article, designed to be pulled forward and engaged with the front section of the article when the article is put in place on a wearer. The tabs typically have included fasteners such as the hook or loop portion of a hook-and-loop fastener, with the other portion of the fastener being on the front section. While such fasteners work well, they are sometimes formed from materials that are relatively stiff and inelastic, conditions that may detract from comfort in use. Also, such fasteners may allow a user, particularly a child, to tamper with the closure. While many developments have been made in the art of absorbent articles to improve performance, there remains a need for further performance improvements in terms of at least one of fit, comfort, and resistance to tampering by the wearer.

SUMMARY OF THE INVENTION

In one aspect, the invention provides an absorbent article including a chassis having a front section and a rear section. The front section or the rear section of the chassis includes a section of first elasticity integral with it or attached to it, a section of second elasticity coupled to the section of first elasticity, and a fastener coupled to the section of second elasticity. The section of first elasticity includes a non-elastic substrate and an elastic material applied in a stretched configuration to the non-elastic substrate to provide the first elasticity.

In another aspect, the invention provides a method of forming an absorbent article. The method includes forming a section of first elasticity integral with or attached to a front section or rear section of a chassis by applying an elastic material to a non-elastic substrate integral with or attached to the front section or rear section. A section of second elasticity is coupled to the section of first elasticity, and a fastener is coupled to the section of second elasticity.

In yet another aspect, the invention provides an absorbent article including a chassis having a front section and a rear section, the front and rear sections of the chassis meeting at a lowest point of the chassis. The absorbent article also includes a front fastener coupled to the front section of the chassis. The rear section of the chassis is configured to engage the front fastener to the rear section of the chassis.

In still another aspect, the invention provides an absorbent article including a chassis having a front section and a rear section, a first engageable portion including a co-adhesive on or attached to the front section, and a second engageable portion including a co-adhesive on a portion of the rear section in position for engagement with the first engageable portion. The first and second engageable portions have in combination a 135° peel strength in a range from about 50 g/in to about 1000 g/in.

In a further aspect, the invention provides an absorbent article including a chassis having a front section and a rear section, a first engageable portion including a co-adhesive on or attached to the front section, and a second engageable portion including a co-adhesive on a portion of the rear section in position for engagement with the first engageable portion. The first and second engageable portions have in combination a 180° shear strength of at least about 1.0 kg/in².

In a yet further aspect, the invention provides a method of producing an absorbent article. The method includes selecting complementary regions on, or attached to, front and rear sections of an absorbent article chassis, the complementary regions configured to be brought into mutually overlapping relationship. A co-adhesive is applied to the complementary regions to thereby provide engageable portions on, or attached to, the front and rear sections such that the engageable portions on or attached to the front and rear sections have in combination a 135° peel strength in a range from about 50 g/in to about 1000 g/in and a 180° shear strength of at least about 1.0 kg/in².

BRIEF DESCRIPTION OF THE DRAWINGS

Exemplary embodiments of the invention will be described with reference to the drawing, of which.

DETAILED DESCRIPTION OF THE INVENTION

Figure 1:
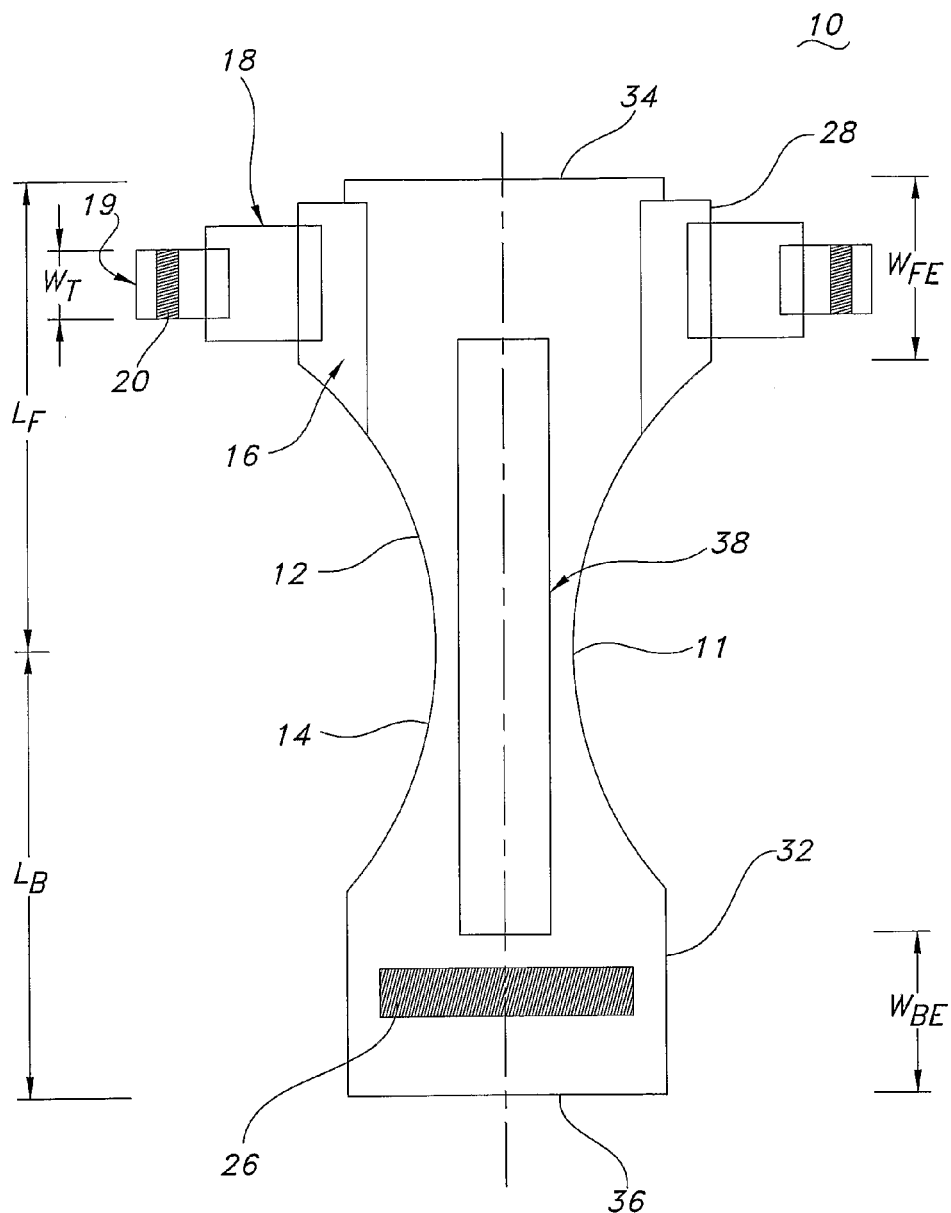
FIG. 1 is a top plan view of an absorbent article according to one exemplary embodiment of the invention.

This application is a U.S. National Phase Application of PCT International Application PCT/US2005/034458 filed on Sep. 28, 2005.

The invention will next be illustrated with reference to the Figures, wherein the same numbers indicate the same elements in all Figures. Such Figures are intended to be illustrative rather than limiting and are included herewith to facilitate the explanation of the present invention. The Figures are not to scale, and are not intended to serve as engineering drawings.

In the exemplary embodiments of the invention selected for illustration in FIGS. 1-5, the absorbent articles 10, 110, 210, 310, 410 are in the form of a diaper. While the following description focuses on diapers with reference to the illustrated embodiments, it should be clear that the subject invention can be used for any type of absorbent article or garment to be worn by a person for trapping urine or menses.

Certain non-limiting aspects of the invention will now be described, with general reference to FIGS. 1-5.

The invention provides an absorbent article 10, 110, 210, 310, 410 including a chassis having a front section 12, 212, 312, 412 and a rear section 14, 214, 314, 414. The front section or the rear section of the chassis may include a section of first elasticity 16, 116, 118, 318, 416 integral with it or attached to it, a section of second elasticity 18, 118, 319, 418 coupled to the section of first elasticity, and a fastener 20, 220, 320, 420 coupled to the section of second elasticity. The section of first elasticity may in some embodiments include a non-elastic substrate and an elastic material applied in a stretched configuration (not shown) to the non-elastic substrate to provide the first elasticity.

Absorbent articles may, in some embodiments, be made by forming a section of first elasticity 16, 116, 118, 318, 416 integral with or attached to a front section 12, 212, 312, 412 or rear section 14, 214, 314, 414 of a chassis by applying an elastic material to a non-elastic substrate integral with or attached to the front section or rear section. A section of second elasticity 18, 118, 319, 418 is coupled to the section of first elasticity, and a fastener 20, 220, 320, 420 is coupled to the section of second elasticity.

The front and rear sections of the chassis meet at a lowest point 11, 211, 311, 411 of the chassis, and the rear section of the chassis is configured to engage the front fastener at a landing zone 26, 226, 326, 426.

The front fastener 20, 220, 320, 420 and the landing zone 26, 226, 326, 426 may each comprise a co-adhesive. In such cases, the absorbent article 10, 110, 210, 310, 410 may be made by selecting complementary regions on, or attached to, the front and rear sections of the chassis and applying the co-adhesive to these complementary regions.

Attention is now drawn to FIG. 1, which is a top plan view of a disposable absorbent article according to the invention. The absorbent article, indicated generally by 10 and seen here from the side of the product that is designed to be in contact with the wearer, includes a front section 12 having a front edge 34 and a rear section 14 having a rear edge 36, the front and rear sections meeting at a lowest point 11 of the absorbent article, i.e., the lowest point of the absorbent article when worn by an individual standing upright.

The front and rear sections 12 and 14 include front and rear ears 28 and 32, respectively, the combination of these with the front and rear sections 12 and 14 constituting a chassis of the absorbent article. In a typical structure according to one embodiment of the invention, lowest point 11 is the narrowest point of the chassis of the absorbent article, and will be located generally at the user's crotch when worn. The front and rear sections 12 and 14 have lengths $L_F$ and $L_B$ and front and rear edges 34 and 36, respectively. An absorbent core 38 is incorporated in the absorbent article 10.

The front section 12 of the absorbent article includes a section of first elasticity 16 on a front ear 28, which has a width $W_{FE}$. A section of second elasticity is provided by an elastic panel 18 coupled to the section of first elasticity 16, and a fastener 20 is coupled to the elastic panel 18 through an intervening tab extension 19 having a width $W_T$. A landing zone 26 suitable for engagement with the fastener 20 is located on rear section 14, which includes a rear ear 32 of width $W_{BE}$. The portions of fastener 20 and landing zone 26 that contact each other will be referred to herein as "engageable portions" of these features. Typically fastener 20 will be of a smaller size than landing zone 26, and hence essentially the entirety of fastener 20 will be engageable, while only that portion of landing zone 26 that contacts fastener 20 is engageable. However, other configurations are contemplated as well.

The landing zone 26 is on a surface of the absorbent article 10 opposite that bearing the absorbent core 38 and fastener 20, so that fastener 20 and landing zone 26 may engage each other when the absorbent article is worn by a user. The landing zone 26 is typically of a rectangular shape, but any shape may be used. There may be a single landing zone configured to receive both fasteners 20, or separate landing zones may provided for each fastener. Although this embodiment of the invention shows the sections of first and second elasticity as being mounted on front section 12, and the landing zone 26 on rear section 14, these positions may be reversed.

Figure 2:
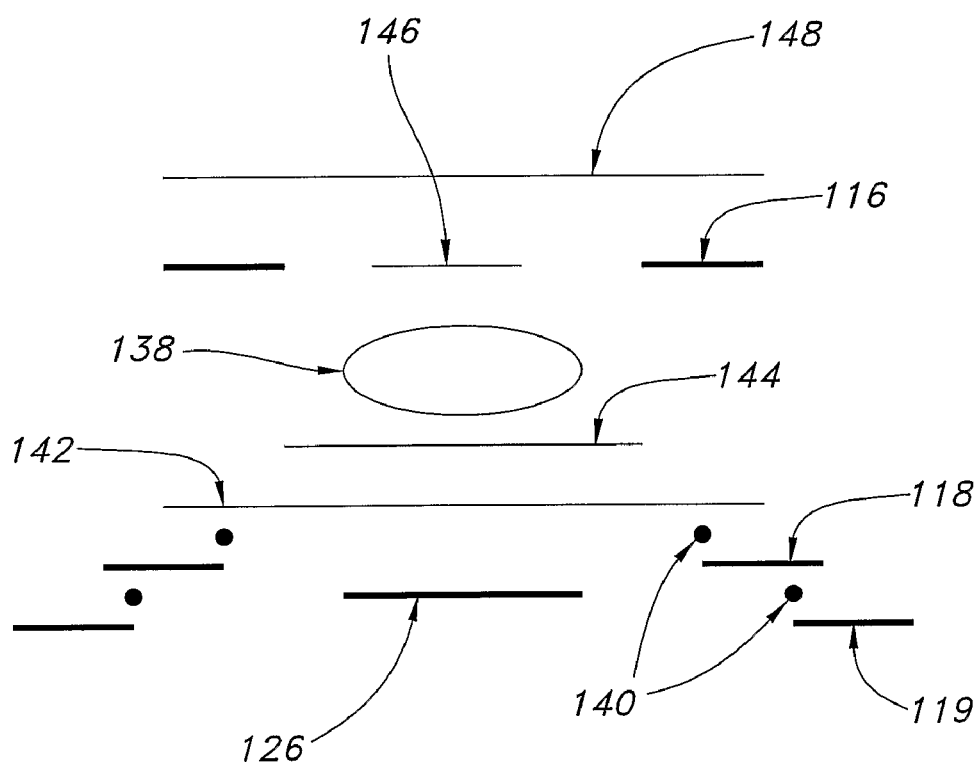
FIG. 2 is an exploded, schematic view of an absorbent article according to another exemplary embodiment of the invention, viewed along the length from one end.

FIG. 2 is an exploded, schematic view of an absorbent article according to an exemplary embodiment of the invention, indicated generally at 110 and viewed lengthwise from one end. The absorbent article 110 includes a liquid permeable topsheet 148 overlying an acquisition layer 146 and bonded to a section of first elasticity 116, which is an elastic material adhered while in a stretched configuration to ears (not shown) on liquid impermeable backsheet 142. The acquisition layer may be, for example, a high basis weight nonwoven or two- or three-dimensional apertured film (or combination thereof).

An absorbent core 138 lies between acquisition layer 146 and a backsheet 142, from which absorbent core 138 is separated by structure 144, which is a fluid-impervious layer (such as polypropylene film). An elastic panel 118, which provides a section of second elasticity, is bonded to an extension tab 119 bearing a fastener (not shown) and to backsheet 142 at points 140. A landing zone 126 is attached to, or integral with, backsheet 142.

The topsheet 148 is arranged to face toward the body of the user, i.e., against the skin of the wearer, when the disposable absorbent article 110 is in place, with the backsheet 142 facing away from the wearer. The topsheet 148 is superimposed over the backsheet 142, with the absorbent core 138 interposed therebetween. The topsheet 148 and/or backsheet 142 can be any suitable shape and dimensions for a design of a disposable absorbent article 110.

The topsheet 148 may be of the same shape as the backsheet 142 or of a different shape, and is bonded to the backsheet 142 at least around the periphery of the absorbent core. The absorbent core 24 is interposed between the topsheet 148 and the backsheet 142. The backsheet 142 and topsheet 148 can be joined together in any suitable manner, e.g., by adhesive bonding. The adhesives may be applied in any manner such as spraying, slot-coat extrusion, printing, or the like. The applied adhesive can be in any desired configuration or design, such as continuous or discontinuous beads, continuous or discontinuous swirls, meltblown patterns, spray patterns or the like. Alternatively, the joining of layers and structure can be accomplished by heat sealing, ultrasonic bonding, or the like.

The backsheet 142 is preferably formed from a laminated sheet of a non-woven material and film (with the non-woven side positioned as the outermost layer). Such material should be hydrophobic, soft in texture, and strong in tensile strength. Suitable materials include a spunbond-meltblown-spunbond (SMS) web having a basis weight of about 10 to 20 grams per square meter (gsm), available from AVGOL Nonwoven Industries LTD., Holon, Israel, and a polypropylene film having a thickness of about 0.4 to 1.0 mils, available from Pliant Corporation, Williamsburg, Va. The spunbond layer is made of polypropylene fibers. Such composites provide the dual advantages of liquid barrier properties of film along with a soft, warm outer fabric texture. The non-woven outer cover can also be made of other suitable cloth-like materials, e.g., spun-bond or thermal-bond non-woven web made of either polypropylene, polyethylene, polyester, bi-component fibers (polyethylene/polypropylene or polyethylene/polyester), or any combinations of these fibers. Various multiple layer configurations or fiber denier variations may be used. Another example includes hydro-entangled non-woven webs, which may contain some cotton and/or rayon fibers blending in with thermal-plastic fibers. Cellulose fibers can also be blended in at small percentages to reduce cost. Still another example is a non-woven outer-cover made of stretchable or elastic materials, such as elastomeric composites of non-woven(s) and elastic membranes or a single layer of elastic material. The elastomeric composite can comprise an inner layer of pre-stretched extruded elastic film sandwiched between and attached to a pair of non-woven webs. The non-woven webs may consist of spun-bond web, thermal-bond web, or a combination of the two. Preferably, the elastic film is made of synthetic rubber and the non-woven made of spun-bond polypropylene.

Other materials for forming the backsheet 142 may include polyethylene films, polypropylene films, co-extruded films (polyethylene and ethylene vinyl acetate), co-polymer films (polyethylene/polypropylene), and polylaminates (polypropylene nonwoven and polyethylene film). Still another example is a film made of a "breathable" microporous polyethylene. Suitable breathable films are available from Tredegar Film Products, Richmond, Va. This material allows water vapor to pass through it over time, while being impervious to liquid water. The water vapor transmission rate may range from 200-2000 grams per square meter per 24-hour period.

In order to enable urine to quickly and efficiently pass through the topsheet 148 and into the absorbent core 138 for trapping therein, the topsheet 148 is preferably liquid permeable. In particular, the topsheet 148 may be selected from a variety of textile-like films and fabrics. Suitable fabrics include non-woven materials that are pervious to liquid, soft and pliable. Preferred non-woven materials include spun-bonded polypropylene, spunbonded polyethylene, and thermally bonded webs of staple fibers, preferably polypropylene shape or sheath/core bi-component fibers having a core of polyester or polypropylene and a sheath of polyethylene. To enhance the fluid control properties of the aforementioned liners, surfactants or wetting agents typified by Triton® X-100 and Triton® X-102 available from Rohm & Haas Company of Philadelphia, Pa. may be applied to the fluid receiving zones of the liner selectively having the outer zones untreated to reduce migration of excreted fluid such as urine into the outer absorbent article 110 regions, leading to leakage. If desired, the topsheet 148 may be formed of a liquid impermeable material having plural apertures or pores extending therethrough so as to make the material liquid permeable.

The absorbent core 38, 138 may be of any shape, but is typically a rectangular member which is centered in the disposable article 10, 110 and which extends from close to the edge 34 of the front section 12 to close to the edge 36 of the rear portion of the absorbent article, as most easily seen in respect to the embodiment of absorbent article 10 shown in FIG. 1. The absorbent core 38, 138 may be made of any suitable absorbent material, as well as combinations of different types of absorbent materials. For example, the absorbent core 38, 138 may be formed of a mixture of pulp fluff and superabsorbent polymer (SAP) wrapped in a liquid permeable tissue wrap (not shown). Examples of SAP include polyacrylamides, polyvinyl alcohol, polyacrylates, various grafted starches, and the like. A desired super absorbent material is a cross-linked polysodium acrylate, which can be purchased from BASF Corporation of Portsmouth, Va., under the trademark ASAP® 2260. The super absorbent materials can be in various geometric forms, such as various shaped particles, fibers, foams, and layers. The fluff and SAP are present in a ratio of about 11 grams of SAP to 16 grams of fluff for a size 4 diaper, and have a core density range of about 0.14 to 0.22 grams per cubic centimeter. The amount of each absorbent material and SAP/fluff ratio depends on the size of the article, e.g., "Small", "Medium", "Large" or "Extra Large."

The absorbent core 38, 138 may be of any shape and may be a single, integral absorbent structure, or can comprise a plurality of individual separate absorbent structures and/or absorbent materials that are operably assembled together. It may also include an air-laid non-woven web that contains super-absorbent particles and/or super-absorbent fibers, polymeric binder and cellulose pulp fibers. In one exemplary embodiment, the absorbent core is sandwiched between two plies of tissue, is aligned on top of the backsheet and adhered with construction adhesive. The tissue may typically have a basis weight of 17 gsm. Suitable tissues are available from Cellu Tissue Corporation, East Hartford, Conn. The absorbent core 38, 138 is typically centered along the transverse direction of the absorbent article 10, 110.

Figure 3A:
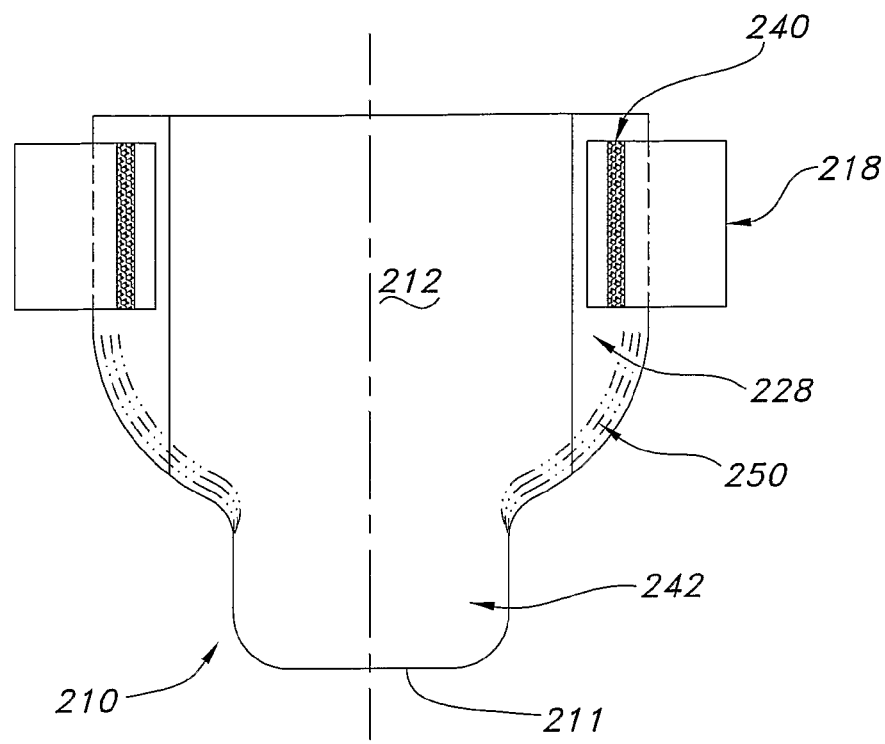
FIGS. 3A and 3B are front and rear views, respectively, of still another absorbent article according to another exemplary embodiment of the invention, folded as for wearing by an individual.
Figure 3B:
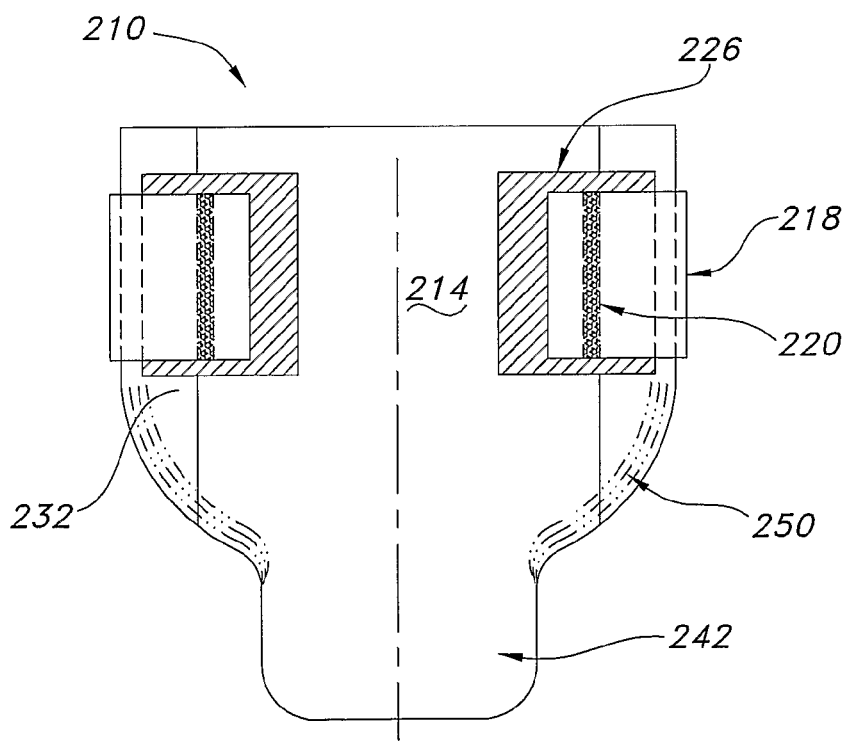

FIGS. 3A and 3B are front and rear views, respectively, of another absorbent article according to the invention, indicated generally at 210, in position for wearing by a user, with in-use lowest point 21 indicated in FIG. 3A. FIG. 3A shows the absorbent article 210 ready for closure of the fasteners on front and rear sections 212 and 214, respectively. An elastic panel 218 is bonded at bond points 240 to front ear 228 on front section 212. In the embodiment shown, elastic panel 218 is bonded to a surface of front ear 228 that is provided by backsheet 242. In this embodiment, elastic panel 218 provides a section of first elasticity, and no section of second elasticity is present. Both the front and rear sections 212 and 214 include optional elastic gathers 250. A fastener 220 (not shown) is on the opposite surface of elastic panel 218 from that shown in FIG. 3A. An absorbent core 238 (not shown) is included in absorbent article 210.

The elastic leg gathers 250 are typically located so that they extend along the leg opening region of the diaper, as disclosed in U.S. Pat. No. 4,695,278 to Lawson and U.S. Pat. No. 4,795,454 to Dragoo. Each gather is elasticized and extends along the side marginal edges of the disposable absorbent article 210.

FIG. 3B shows the rear section 214 of absorbent article 210 with fastener 220 (viewed here through the outer surface of elastic panel 218) engaged with a landing zone 226, as the fastener would be engaged when the absorbent article is worn by a user. Typically, the portion of elastic panel 218 that extends beyond fastener 220, and which may be used for grasping the panel 218 when engaging or disengaging it from landing zone 226, is not elastic. In the embodiment shown, landing zone 226 is attached to rear section 214 such that it is partly attached to rear ear 232 and partly attached to the non-ear portion of rear section 214. However, the landing zone 226 may be attached entirely to either of these areas.

In some embodiments of the invention, the absorbent article is designed such that the front section of the article wraps around the user's waist and attaches to the rear section toward the rear of the user, rather than an arrangement where the back section wraps around and attaches at the user's front. Although not explicitly shown in FIG. 1, absorbent articles designed for back attachment optionally include a chassis where the front section has a length $L_F$ that is shorter than the length $L_B$ of the rear section, with the front and rear sections meeting at the crotch of the wearer at a lowest point, for example as shown at 11 in FIG. 1. It has been discovered that a product that attaches in the rear may be of particular benefit in the toilet training of children, by helping to avoid tampering by the child.

Figure 4A:
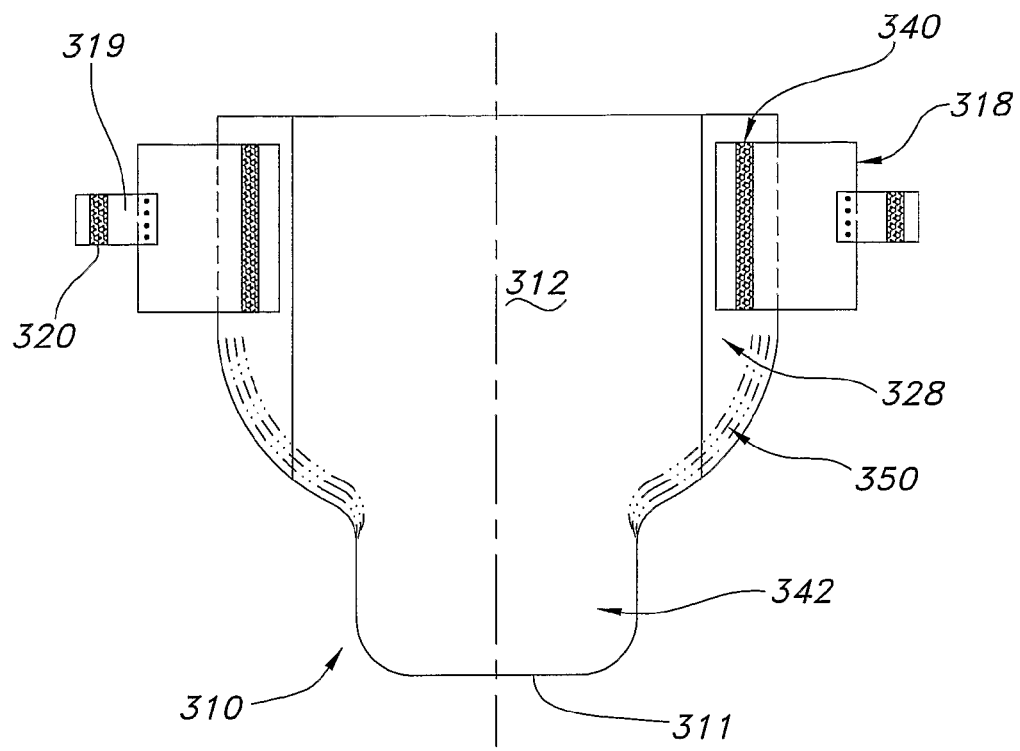
FIGS. 4A and 4B are front and rear views, respectively, of yet another absorbent article according to another exemplary embodiment of the invention, folded as for wearing by an individual.
Figure 4B:
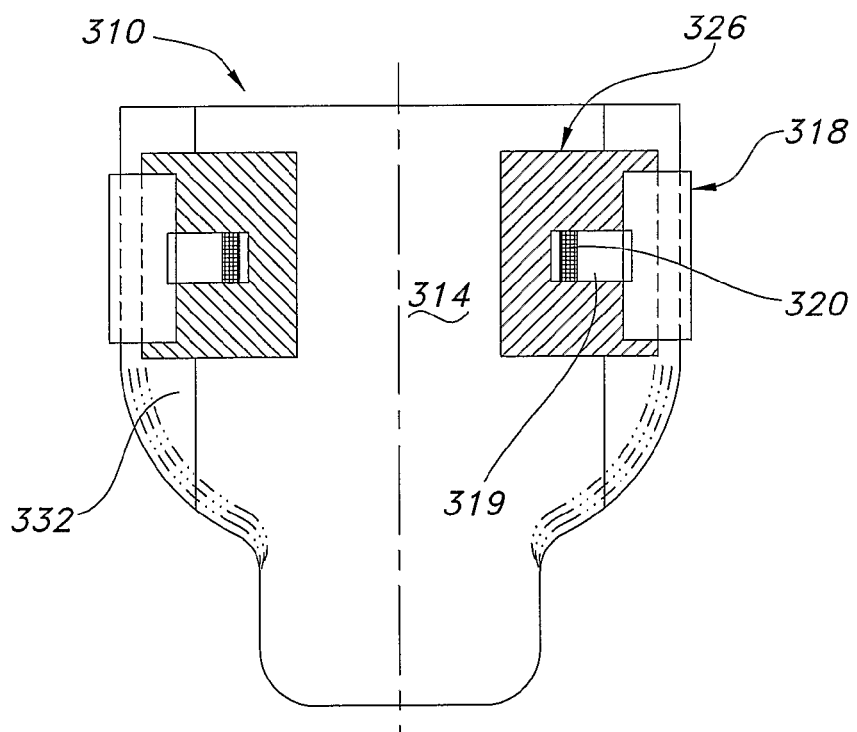

FIGS. 4A and 4B are front and rear views, respectively, of another absorbent article according to the invention, indicated generally at 310, in position for wearing by a user, with in-use lowest point 311 indicated in FIG. 4A. FIG. 4A shows the absorbent article 310 ready for closure of the fasteners on front and rear sections 312 and 314, respectively. An elastic panel 318 is bonded at bond points 340 to front ear 328 on front section 312. In the embodiment shown, elastic panel 318 is bonded to a surface of front ear 328 that is provided by backsheet 342. Both the front and rear sections 312 and 314 include optional elastic gathers 350. A fastener 320 is on an elastic tab extension 319 (viewed here through the surface of tab extension 319), which is in turn attached to the elastic panel 318, thereby providing two sections of elasticity. An absorbent core 338 (not shown) is included in absorbent article 310.

FIG. 4B shows the rear section 314 of absorbent article 310 with fastener 320 (viewed here through the outer surface of elastic tab extension 319) engaged with landing zone 326, as the fastener would be engaged when the absorbent article is worn by a user. Typically, the portion of elastic tab extension 319 that extends beyond fastener 320, and which may be used for grasping the tab extension 319 when engaging or disengaging it from landing zone 326, is not elastic. In the embodiment shown, landing zone 326 is attached to rear section 314 such that it is partly attached to rear ear 332 and partly attached to the non-ear portion of rear section 314. However, the landing zone 326 may be attached entirely to either of these areas.

In some embodiments of the invention, the closure mechanism for the absorbent article optionally includes a dual elastic structure, with sections of greater and lesser elasticity attached in series to each other. By providing such an arrangement, it has been found that a more comfortable fit may be obtained, as well as reduced drooping of the product in use and greater flexibility in fitting the product to an individual, thereby reducing the number of sizes needed. Optionally, the absorbent article may be sold in an already-closed configuration, so that the user dons the article by stepping through and pulling up like a normal non-absorbent undergarment. The dual elastic feature allows for ease of stretching the waist closure to fit the user, yet provides additional stretching capacity if needed.

Figure 5A:
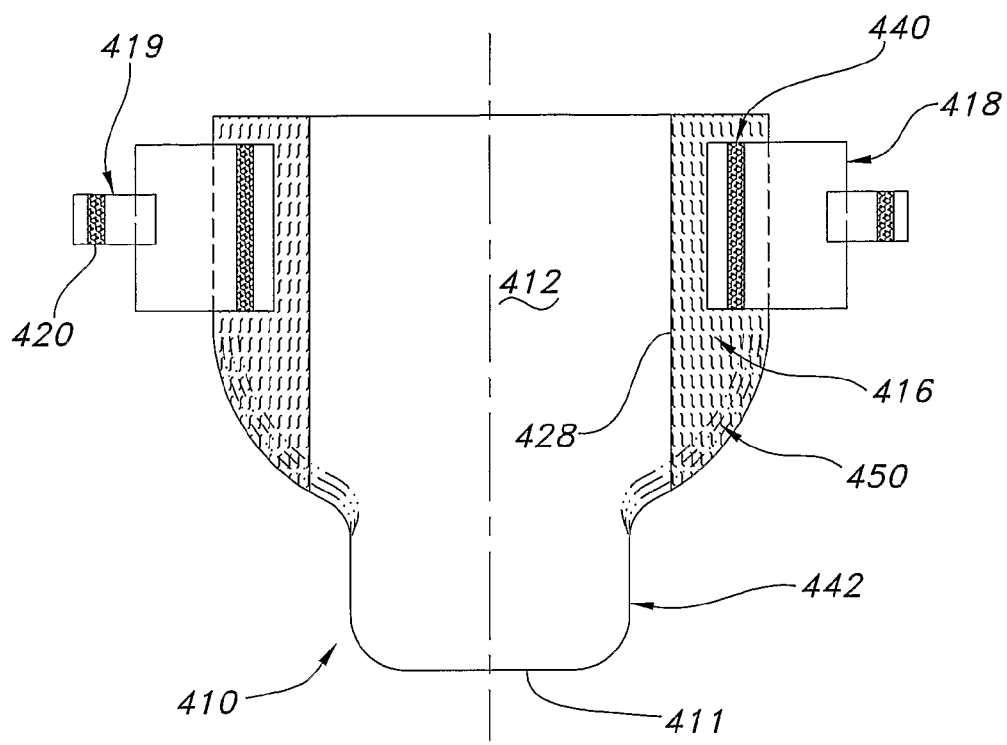
FIGS. 5A and 5B are front and rear views, respectively, of a still further absorbent article according to another exemplary embodiment of the invention, folded as for wearing by an individual.
Figure 5B:
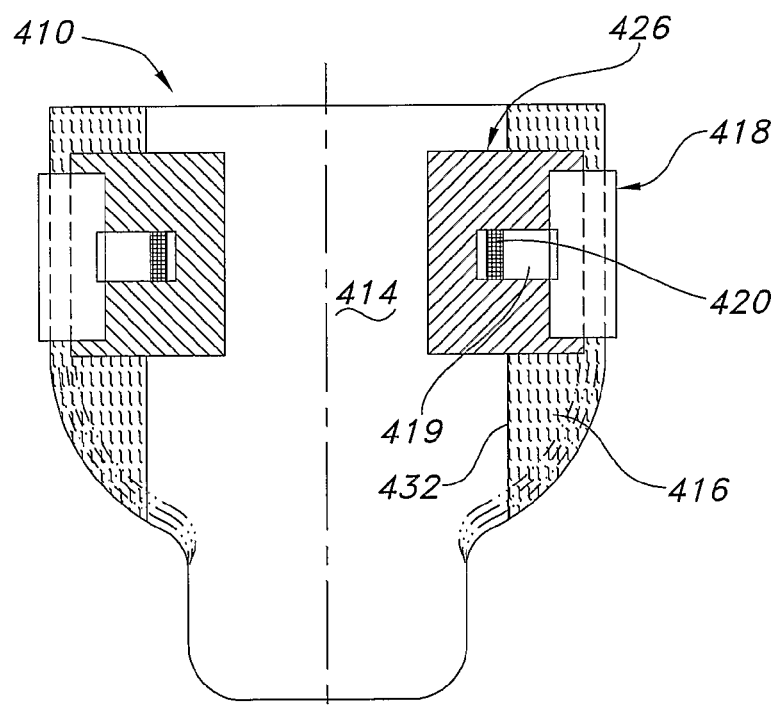

FIGS. 5A and 5B are front and rear views, respectively, of another absorbent article according to the invention, indicated generally at 410, in position for wearing by a user, with in-use lowest point 411 indicated in FIG. 5A. FIG. 5A shows the absorbent article 410 ready for closure of the fasteners on front and rear sections 412 and 414, respectively. An elastic panel 418 is bonded at bond points 440 to front ear 428 on front section 412. In the embodiment shown, elastic panel 418 is bonded to a surface of front ear 428 that is provided by backsheet 442. Front ear 428 is made of an elastic material, providing a second section of elasticity. Both the front and rear sections 412 and 414 include optional elastic gathers 450. A fastener 420 is on a non-elastic tab extension 419 (viewed here through the surface of tab extension 419), which is in turn attached to the elastic panel 418. An absorbent core 438 (not shown) is included in absorbent article 410.

FIG. 5B shows the rear section 414 of absorbent article 410 with fastener 420 (viewed here through the outer surface of elastic tab extension 419) engaged with landing zone 426, as the fastener would be engaged when the absorbent article is worn by a user. In the embodiment shown, landing zone 426 is attached to rear section 414 such that it is partly attached to rear ear 432 and partly attached to the non-ear portion of rear section 414. However, the landing zone 426 may be attached entirely to either of these areas.

When the disposable absorbent article 10 is in place on the person with the front section 12 disposed over the lower abdomen, the rear section 14 over the lower back and buttocks region, and lowest or narrowest point 11 defining a crotch between the legs, each fastener 20 may be brought into engagement with a portion of the landing zone 26 closest to each fastener to releasably secure the tab extension 19 thereto.

Dual Elasticity

In some embodiments of the invention, for example those depicted in FIGS. 1, 2, 4, and 5, two sections of elasticity are provided in parts of the absorbent article that connect the front and rear sections. In the embodiments shown in the Figures, the sections of first and second elasticity are shown attached to the front section of the absorbent article, but they may instead be attached to the rear section. In each of these embodiments, one of the elastic sections is an elastic panel 18, 118, 318, 418, while the other may be either an elastic portion 16, 116, 416 on an ear, or an elastic tab extension 319. In all cases, the elastic section closer to the center line of the absorbent article is referred to herein as the "section of first elasticity", while the more outward one is referred to the "section of second elasticity." Thus in the embodiment of FIGS. 1, 2, and 5 the elastic panel provides the section of second elasticity, while in FIG. 4 it provides the section of first elasticity.

In some embodiments of the invention, the section of first elasticity 16 comprises an elastic material applied in a stretched configuration to a non-elastic substrate, which may for example be a polyolefin or other material used to form a backsheet for the absorbent article 10. Exemplary elastic materials include elastic films, foams, and nonwoven materials, suitable examples and methods of application of which are known in the art. Examples include Fabriflex® stretch nonwoven film laminate, available from Tredgar Corporation of Richmond, Va., or polyurethane foam laminate, available from General Foam Corporation of Paramus, N.J. Such a configuration is seen for example in FIG. 5, where such materials are on the ears of the absorbent article. This section is subsequently (or previously, before application of the stretched elastic material) coupled to the section of second elasticity, typically an elastic panel 18, 118, 418. The elastic panel may comprise any of a number of elastic materials known in the art, with typical exemplary materials being high-stretch laminates having an elastic middle layer sandwiched between two cloth-like outer layers, such as Fabriflex® film laminate.

In other embodiments of the invention, such as shown in FIG. 4, elastic panel 318 is the section of first elasticity, and is connected to an elastic tab 319 that provides the section of second elasticity. The elastic tab 319 may comprise any of a number of elastic materials known in the art, with typical exemplary materials being Tredtab material, available from Tredgar Corporation.

Regardless of which parts of the absorbent article provide the sections of first and second elasticity, the relative elasticities are preferably such that the section of first elasticity reaches its maximum stretched extension at a pulling force that is lower than that at which the section of second elasticity is fully extended. Thus, once the first section is fully extended, the second section begins or continues to stretch, thereby providing a dual stretch character. Typically, the force to full extension of the second elasticity section is about two to five times that of the first section.

By providing a product with sections of first and second elasticities, especially when those elasticities are within the ranges set forth above, it has been found that a more comfortable fit may be obtained, as well as reduced drooping of the product in use and greater flexibility in fitting the product to an individual, thereby reducing the number of sizes needed to be kept in inventory. Dual elasticity may provide advantages when additional stretching force is applied to the closure, for example when the belly of the wearer bulges when he/she sits down.

Rear Engagement of Fasteners

In some embodiments of the invention, for example as shown in FIG. 1, the absorbent article is configured such that coupling of front and rear fasteners occurs in the rear of the absorbent article as worn by a user. The front and rear sections of an absorbent article according to the invention may be identified by reference to the relative lengths $L_B$ and $L_F$ of rear section 14 and front section 12, respectively, referring to FIG. 1. The lengths $L_B$ and $L_F$ are determined relative to a lowest point 11 of the article as worn by a user, that point typically being a narrowest point of the absorbent article, with $L_B$ being greater than $L_F$. In some embodiments of the invention, the front and rear sections each comprise an ear, such as seen in FIG. 1 at 28 and 32, respectively, and in such cases the width $W_{BE}$ of the rear ear is greater than the width $W_{FE}$ of the front ear. In some embodiments of the invention, the front section of the absorbent article 10, 110, 210, 310, 410, 510 has a greater absorbent capacity than the rear portion, for example by providing a greater basis weight of a superabsorbent material in the front vs. the rear portion of the absorbent core 38, 138, 238, 338, 448.

It has been discovered that a product that attaches in the rear may be of particular benefit in the toilet training of children, by helping to avoid tampering by the child. Further, rear closure may reduce the potential for scratching or other skin irritation by the components of the closure system, for example when the wearer bends forward at the waist to sit or stoop.

Fastener Types

In some embodiments of the invention, the fastener on the front section and the landing zone on the rear section (or vice versa) of the absorbent article are hook-and-loop fasteners, such as are known in the art. Either the hook or the loop portion of the fastener may be on the front section 12, 212, 312, 412, with the other being on the rear section 14, 214, 314, 414. Any suitable multi-hook and multi-loop materials may be used. Particularly suitable multi-hook patches are available from YKK (U.S.A.), Inc., Marietta, Ga. under the model designation Microhook (D-7) or Macrohook (EL "B"), while a particularly suitable multiloop material is a polyester fiber material having a basis weight of 1.55 ounce per square yard with a laminated polypropylene film (8 mil.) backing, available from FAB Industries, Inc., New York, N.Y.

In other embodiments, the fastener on the front section may be an adhesive on tab extension 19, 119, 319, 419 or on elastic panel 218, with the complementary fastener being a receptive area on the landing zone 26, 126, 326, 426, or 226. Alternatively, the positions of the adhesive and the receptive area may be reversed. Suitable exemplary adhesive tapes are available from 3M Corporation, St. Paul, Minn., and the landing zone may be formed of a polyester film with a pre-applied adhesive in a selected print pattern, such as also available from 3M Corporation.

In some preferred embodiments of the invention, both the receptive area and the fastener comprise a co-adhesive, thereby providing a re-fastenable garment. It has been discovered that co-adhesives providing material properties within certain ranges are particularly suitable for making absorbent articles with a high level of comfort for the wearer, as well as ease of donning and doffing the product without tearing of the garment or, instead, inadvertent disengagement of the fasteners. Thus the absorbent articles of this invention have closures that are re-fastenable.

It has been discovered that products where the combined engaged area of the two co-adhesive bearing sections has a 135° peel strength in a range from about 50 g/in to about 1000 g/in are especially suitable, as determined by ASTM D 5170-98 Standard Test Method for Peel Strength ("T" Method) Hook and Loop Touch Fasteners. For purposes of this invention, the test method is modified by using a RD-3000 Roll-down machine (available from ChemInstruments Inc., Fairfield, Ohio) with 454 g (1 lb.)+/−5 g, instead of the hand roller in the Test Method which uses 11 lbs under ambient laboratory conditions. Peel strengths that are too low may result in accidental disengagement of the fastener, while excessive peel strength may result in tearing of the absorbent article when the fastener is removed. Typically, the peel strength will be from about 100 g/in to about 800 g/in, more typically 200 g/in to about 600 g/in, and even more typically from about 400 g/in to about 500 g/in.

It has also been found that a 180° shear strength of the combined engaged area of at least about 1.0 kg/in$^2$ is desirable, as determined by ASTM D 51169-98 Standard Test Method for Shear Strength (Dynamic Method) of Hook and Loop Touch Fasteners, using the same modifications as described above for peel strength measurement. If the shear strength of the closure is too low, it may fail due to the pulling action provided by the one or two sections of elasticity, which are typically stretched in use and thus exert a force on the closure. Typically, the shear strength will be at least about 2.5 kg/in$^2$, and more typically at least about 5.0 kg/in$^2$.

It has further been discovered that a reduced compression modulus (measured in psi) as determined by ASTM D695 is desirable. The compression modulus of the combined engageable portions of the closure relates to the stiffness of the closure, with the two increasing or decreasing together. More specifically, the compression modulus of the combined components of the absorbent article at the location of engagement of the engageable portions (i.e., at the location of the fastening mechanism) has been discovered to be beneficially reduced. For example, at the point of engagement, the components of the engaged region may include a layer of co-adhesive, a top sheet, a bottom sheet, and a layer of adhesive binding the top and bottom sheets from the front portion of the absorbent article and a layer of co-adhesive, a top sheet, a bottom sheet, and a layer of adhesive binding the top and bottom sheets from the back portion of the absorbent article (i.e., eight layers). Alternatively, for example, the components of the engaged region may include only a layer of co-adhesive and a substrate (e.g., a tab component, a top sheet, or a cover sheet) from the front portion of the absorbent article and a layer of co-adhesive and a substrate from the back portion of the absorbent article (i.e., four layers). Other layers (including fewer and more layers) are contemplated as well. The number and type of layer components at the engaging region depends of course on the construction of the absorbent article and its intended use.

As a matter of comfort for the wearer, it is advantageous to provide as low as possible a level of stiffness, to prevent skin irritation or other discomforts. It has been discovered that such reduced stiffness can be accomplished by reducing the compression modulus of the absorbent article at the location where front and back portions of the article are joined or fastened. It has further been discovered that, by reducing or controlling the compression modulus of the fastener mechanism, the degree to which the fastener mechanism contributes to the overall stiffness of the absorbent product can also be reduced or controlled.

The use of co-adhesives to fasten the products of this invention provides certain advantages. For example, co-adhesive surfaces only stick to each other, and the combined surfaces typically provide improved softness, flexibility, and comfort to the wearer. Surfaces joined by co-adhesives are typically quiet when separated, and in many cases co-adhesive-based fastener systems are relatively inexpensive to incorporate into the product as compared with other types of fasteners.

Co-adhesives suitable for use according to the invention may be of any of a variety of types, and their application may involve UV curing, extrusion of the co-adhesive onto the product, and/or assembly of pre-made co-adhesive components onto the product. Examples of suitable co-adhesives include #8819-29-B, available from National Starch in Bridgewater, N.J. Suitable co-adhesives may also be procured from other manufacturers.

Based on the parameters set forth herein, suitable co-adhesives can be readily formulated. Specifically, for example, a suitable co-adhesive can be readily formulated based on specifications for peel strength, shear strength, and/or other parameters.

In certain preferred embodiments of the invention, tab extensions 19, 119, 319, 419 have a width $W_T$ that is at least 12% of the combined front and rear section lengths $L_F$ and $L_B$. Typically, the width will be at least 15% of the combined section lengths. It has been found that, when tab extensions meet these conditions, the engaged fastener and landing zone assembly is such that the fit and feel of the absorbent article in use resembles that of a typical non-absorbent undergarment.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An absorbent article comprising:
   a chassis having a front section and a rear section, said front section or said rear section of said chassis including a section of first elasticity integral therewith or attached thereto, a section of second elasticity coupled to said section of first elasticity, and a fastener coupled to said section of second elasticity, a lateral end of the section of second elasticity extending beyond a lateral end of the section of first elasticity;
   said section of first elasticity comprising a non-elastic substrate and an elastic material applied in a stretched configuration to said non-elastic substrate to provide said first elasticity.

2. The absorbent article recited in claim 1, said elastic material being formed from a film, a foam, or a non-woven material.

3. The absorbent article recited in claim 1, further comprising at least one fastener coupled to said rear section or said front section of said chassis and positioned for engagement with said fastener coupled to said section of second elasticity.

4. A method of forming an absorbent article, said method comprising the steps of:
   forming a section of first elasticity integral with or attached to a front section or rear section of a chassis by applying an elastic material to a non-elastic substrate integral with or attached to the front section or rear section;
   coupling a section of second elasticity to the section of first elasticity so that a lateral end of the section of second elasticity extends beyond a lateral end of the section of first elasticity; and
   coupling a fastener to the section of second elasticity.

5. The method recited in claim 4, said step of forming the section of first elasticity comprising applying a film, a foam, or a non-woven material in a stretched configuration to the non-elastic substrate to provide the first elasticity.

6. The method recited in claim 4, further comprising the step of coupling at least one fastener to the rear section or front section of the chassis for engagement with the fastener coupled to the section of second elasticity.

7. An absorbent article comprising:
   a chassis having a front section and a rear section;
   said front section of said chassis including a section of first elasticity, a section of second elasticity coupled to said section of first elasticity, and a first engageable portion comprising a co-adhesive on said section of second elasticity, said section of first elasticity comprising a non-elastic substrate and an elastic material applied in a stretched configuration to said non-elastic substrate to provide said first elasticity, a lateral end of the section of second elasticity extending beyond a lateral end of the section of first elasticity;
   said rear section of said chassis including a second engageable portion comprising a co-adhesive in position for engagement with said co-adhesive of said first engageable portion on said section of second elasticity; and
   said first and second engageable portions having in combination a 135° peel strength in a range from about 50 g/in to about 1000 g/in and a 180° shear strength of at least about 1.0 kg/in$^2$.

8. The absorbent article recited in claim 7, wherein the 135° peel strength is in a range from about 200 g/in to about 600 g/in.

9. The absorbent article recited in claim 7, wherein the 180° shear strength is least about 2.5 kg/in$^2$.

* * * * *